(12) United States Patent
Kaneyama et al.

(10) Patent No.: US 9,220,519 B2
(45) Date of Patent: Dec. 29, 2015

(54) BONE RESECTION JIG USED IN ARTIFICIAL KNEE JOINT REPLACEMENT SURGERY

(75) Inventors: Ryutaku Kaneyama, Kisarazu (JP); Koichi Kuramoto, Okayama (JP); Keitarou Yamamoto, Okayama (JP); Daisuke Maruyama, Okayama (JP)

(73) Assignees: NAKASHIMA MEDICAL CO., LTD., Okayama-Ken (JP); Ryutaku Kaneyama, Chiba-Ken (JP)

(*) Notice: Subject to any disclaimer, the term of this patent is extended or adjusted under 35 U.S.C. 154(b) by 158 days.

(21) Appl. No.: 13/822,574

(22) PCT Filed: Sep. 13, 2011

(86) PCT No.: PCT/JP2011/071537
§ 371 (c)(1),
(2), (4) Date: Mar. 12, 2013

(87) PCT Pub. No.: WO2012/036298
PCT Pub. Date: Mar. 22, 2012

(65) Prior Publication Data
US 2013/0184714 A1 Jul. 18, 2013

(30) Foreign Application Priority Data
Sep. 13, 2010 (JP) .................. 2010-203873

(51) Int. Cl.
*A61B 17/17* (2006.01)
*A61B 17/02* (2006.01)
(Continued)

(52) U.S. Cl.
CPC ........... *A61B 17/1764* (2013.01); *A61B 17/025* (2013.01); *A61B 17/155* (2013.01); *A61F 2/4684* (2013.01); *A61B 2017/0268* (2013.01); *A61F 2/389* (2013.01)

(58) Field of Classification Search
CPC ................................. A61B 17/1764
USPC ............................. 606/86 R, 87–90
See application file for complete search history.

(56) References Cited

U.S. PATENT DOCUMENTS

| 5,520,695 A | 5/1996 | Luckman |
| 7,678,115 B2 * | 3/2010 | D'Alessio et al. ........ 606/88 |

(Continued)

FOREIGN PATENT DOCUMENTS

| EP | 1 442 711 A | 8/2004 |
| FR | 2810227 A | 12/2001 |

(Continued)

*Primary Examiner* — Christian Sevilla
(74) *Attorney, Agent, or Firm* — DLA Piper LLP (US)

(57) ABSTRACT

A bone resection jig that can make ligament tension equal at extension and flexion positions without any actual measurements when resecting femur and tibia during artificial knee joint replacement surgery. The bone resection jig used in artificial knee joint replacement surgery includes a spacer block (1) comprised of a grip (6), a hollow box (7) that is provided on an other end side of the grip and has a vertical hole (7a) therein, and a reference spacer part (8) that extends out from the hollow box (7) and is adapted be inserted into the resection region between femur and tibia; a reference pin guide (2) which, when the femur and tibia are in the flexion position, is inserted into the vertical hole (7a) of the hollow box, extends on the reference spacer part (8) to the other end side of the grip so as to come into contact with a resection plane ($F_H$) of the tip of the distal end of the femur, and is formed with guide holes (9) for guiding reference pins (3) to be installed from a front side into the resection plane ($F_H$) of the tip of the distal end of the femur; and an aiming member (12) which is, after the spacer block (1) has been removed from a space between the femur and tibia leaving the reference pins (3), brought onto the reference pins (3) by being guided thereby, the aiming member being provided with an indicator (14) that indicates a resection plane ($F_R$) at a back of the distal end of the femur when the aiming member (12) comes into contact with the resection plane ($F_H$) of the tip of the distal end of the femur.

7 Claims, 8 Drawing Sheets

(51) Int. Cl.
*A61B 17/15* (2006.01)
*A61F 2/46* (2006.01)
*A61F 2/38* (2006.01)

(56) References Cited

U.S. PATENT DOCUMENTS 7,708,741 B1 * 5/2010 Bonutti .................. 606/86 R
8,721,568 B2 * 5/2014 Rock et al. .................. 600/595

2004/0249387 A1 * 12/2004 Faoro .................. 606/88
2005/0143744 A1 * 6/2005 Keeven et al. .................. 606/86
2007/0293868 A1 * 12/2007 Delfosse et al. .................. 606/88
2010/0305575 A1 * 12/2010 Wilkinson et al. .................. 606/88

FOREIGN PATENT DOCUMENTS

JP    H11-313844 A    11/1999
JP    2007-75517 A    3/2007

* cited by examiner

BONE RESECTION JIG USED IN ARTIFICIAL KNEE JOINT REPLACEMENT SURGERY

TECHNICAL FIELD

The present invention relates to a bone resection jig used during artificial knee joint replacement surgery.

BACKGROUND ART

When a knee joint suffers knee osteoarthritis, rheumatoid arthritis, or bone tumors, or suffers external injury or the like, the part subject to joint damage at the tips of the femur and tibia is resected, and those parts are replaced with an artificial joint. This artificial knee joint, as conventionally seen, comprises a combination of a femur component, which has two condyles of medial and lateral, and a tibia component, which has a joint plate that bears these two condyles and allows them to rotate; and it is desirous that artificial knee joints that are comprised of such condyles and joint plates preferably be movable similarly to a biogenic knee joint.

The femur and tibia are connected by numerous ligaments, and extension and flexion of them are made by tensioning and relaxing these ligaments. It is particularly desirable that when tensioning occurs tension be the same when in the extension position and when in the flexion position, and it is also desirable that flexion movement be smooth accompanying no pain. Also, since Japanese people often sit with their legs folded beneath them, it is necessary that deep flexion is possible. With these situations in mind, Patent Literature 1, listed below, proposes a bone resection jig that sets a bone resection range after confirming that tension is the same in the extension position and in the flexion position.

However, the invention of this prior art checks (measures) the tension of ligaments in both extension and flexion positions; accordingly, the operation is troublesome, and it requires a longer surgical time. Further, the constitution is complex, and it includes many moving parts and adjustment parts, and further it requires numerous operation steps that are difficult and require proficiency. In addition, it is heavy and expensive.

PRIOR ART DOCUMENTS

Patent Literature

Patent Literature 1: Patent Application Laid-Open (Kokai) 2007-75517

SUMMARY OF THE INVENTION

Problems the Invention Attempts to Solve

The present invention proposes a bone resection jig based on the principle that the same tension can be derived in ligaments at the extension position and flexion position if the bone resection range (interval) is the same at both positions, and it provides a bone resection jig which is extremely simple in constitution and inexpensive. Furthermore, the present invention provides a bone resection jig that does not require proficiency to operate, can shorten surgery time, and reduces the impact on a patient.

Means to Solve the Problems

Given the problems above, the present invention is to provide a bone resection jig as claimed in claim 1 which is for an artificial knee joint replacement surgery and is used when a back of a distal end of a femur in a flexion position is resected after a tip of the distal end of the femur and a tip of a proximal end of a tibia in an extension position are resected horizontally, and this bone resection jig includes: a spacer block comprised of a grip, a hollow box that is provided on an other end side of the grip and has a vertical hole therein, and a reference spacer part that extends out from the hollow box and is adapted be inserted into the resection region between femur and tibia; a reference pin guide which, when the femur and tibia are in the flexion position, is inserted into the vertical hole of the hollow box, extends on the reference spacer part to the other end side of the grip so as to come into contact with a resection plane of the tip of the distal end of the femur, and is formed with guide holes for guiding reference pins to be installed from a front side into the resection plane of the tip of the distal end of the femur; and an aiming member which is, after the spacer block has been removed from a space between the femur and tibia leaving the reference pins, brought onto the reference pins by being guided thereby, the aiming member being provided with an indicator that indicates a resection plane at a back of the distal end of the femur when the aiming member comes into contact with the resection plane of the tip of the distal end of the femur.

Further, in regards to the above-described bone resection jig, the present invention provides: a means as recited in claim 2 wherein the axis of the grip passes through the center of the reference spacer part while the area around the hollow box of the grip is offset relative to the axis to a position that can avoid interfere with the patellar tendon; a means as recited in claim 3 wherein the resection plane of the tip of the distal end of the femur can be set at a right angle, obtuse angle or acute angle with respect to the resection plane of the back of the distal end of the femur; a means as recited in claim 4 wherein two guide holes horizontally left and right are provided; a means as recited in claim 5 wherein the indicators are through-holes that are formed in the aiming member at a variety of levels and angles; and a means as recited in claim 6 wherein one or a plurality of additional spacers are put on another on the reference spacer part of the spacer block for measuring the distance of the resected distal end of the femur and the resected proximal end of the tibia in the extension position.

Effects of the Invention

According to the bone resection jig of the present invention of claim 1, the primary constituent parts are extremely few in number, which are a spacer block to be inserted into the resection region of the femur and tibia, a reference pin guide that appropriately sets the flexion position, and an aiming member that sets the resection range for the back of the distal end of the femur; and the constitution of the various constitutional elements of these parts is also simple. Accordingly, the bone resection jig of the present invention has a small number of constituent parts, is light in weight and inexpensive, and is simple in operation, thus not requiring a great deal of skill to operate.

According to the means of claim 2, the hollow box does not block the field of view when the spacer block is inserted. According to the means of claim 3, the angle between the tip and back of the distal end of the femur can be matched to the shape of the femur side part of the artificial knee joint, and thus the femur side part can be inserted accurately and securely. According to the means of claim 4, the reference pin guide can be set accurately in the right attitude, which is horizontal. According to the means of claim 5, the back of the distal end of the femur can be set to resection planes of a variety of levels and angles. According to the means of claim 6, the femur can be placed in flexion of 90° with the reference spacer part of the spacer block left inserted after a prescribed amount of the distal end of the femur and the proximal end of the tibia are resected.

MODES FOR CARRYING OUT THE INVENTION

Figure 1:
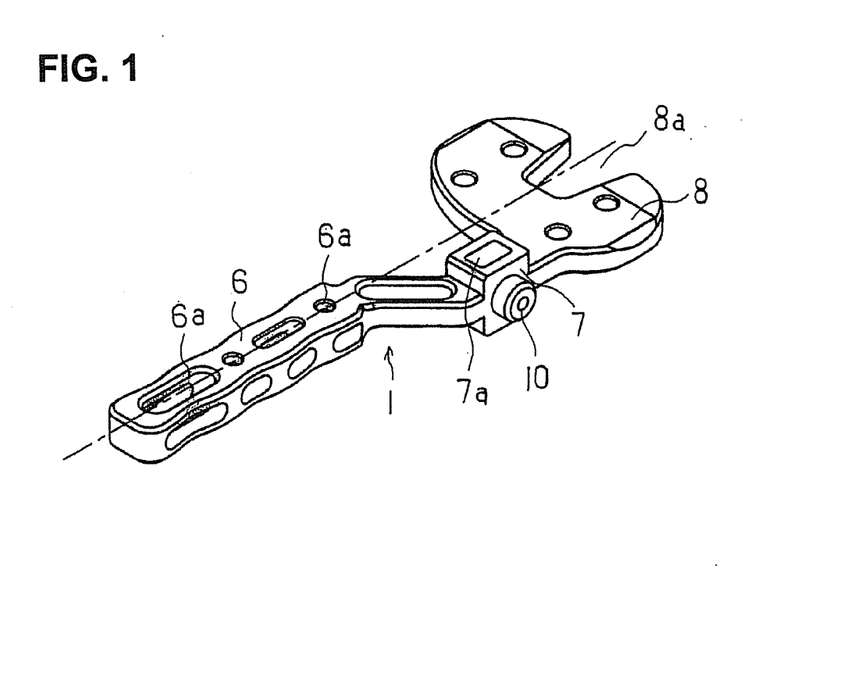
FIG. 1 A perspective view of the spacer block.
Figure 2:
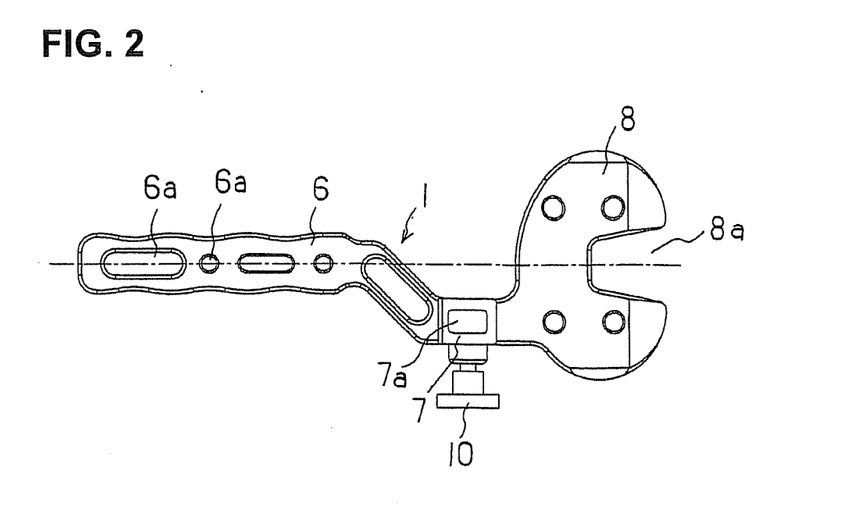
FIG. 2 A top view of the spacer block.
Figure 3:
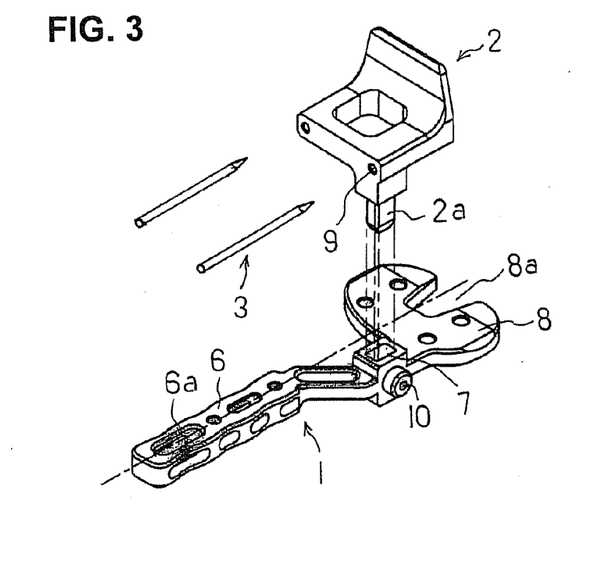
FIG. 3 A perspective view showing a relationship between the spacer block, reference pin guide, and reference pins.

Modes for carrying out the present invention will be described below with reference to the drawings. FIG. 1 is a perspective view of a spacer block 1 that comprises a main body of the bone resection jig (hereafter, called "the jig") used during artificial knee joint replacement surgery in accordance with the present invention, FIG. 2 is a top view, and FIG. 3 is a perspective view of the spacer block 1, a reference pin guide 2, and reference pins 3. In the following, reference is made to front/back, up/down, and left/right directions. These are in reference to the knee in standing position and seen from the front and lateral sides. "Front" refers to the front of the knee (the patella side), and "upper" refers to the femur side; and for "left/right" the left side is a lateral side in the case of the left knee.

The spacer block 1 is one that is inserted into a resection region of a resected distal end of a femur 4 and a resected proximal end of a tibia 5, and it supports the reference pin guide 2. The spacer block 1 is comprised of, from the front to the back, a grip 6, a hollow box 7 that has a perpendicular vertical hole 7a, and a reference spacer part 8. The grip 6 is a handle held by a surgeon, and it is provided with a plurality of vertical holes 6a in its middle portion for making alignment with the leg. The vertical hole 7a of the hollow box 7 is for inserting therein the reference pin guide 2, and it is square so that the reference pin guide 2 is not rotated inside. The reference pin guide 2 is supported when its base 2a is inserted into the vertical hole 7a of the hollow box 7. The reference pin guide 2 is a guide for bending the tip of the distal end of the femur 4 by 90° relative to the tip of the proximal end of the tibia 5 and further for inserting the reference pins 3 to the femur, and thus it is equipped with guide holes 9 for that purpose.

In the above structure, though the axis of the grip 6 passes through the center of the reference spacer part 8, the hollow box 7 is offset from the axis. The reason for this offsetting of the hollow box 7 is that it is set directly in front of the knee joint to increase the sighting performance of the aiming member, which will be described below, that is mounted on it, thus the vicinity of the hollow box 7 of the grip 6 is offset from the axis to hold it in a position that does not interfere with the line of sight on or manipulations of the patellar tendon (and holds the patellar tendon off center on the outside). The reference pin guide 2 is, for this reason, off-center with respect to the axis side relative to the base 2a; and thus when the base 2a of the reference pin guide 2 is inserted into the vertical hole 7a of the hollow box 7, the reference pin guide 2 fully faces the reference spacer part 8.

In addition, a cut-out 8a is made in the front tip (or, with respect to the knee, in the back) of the reference spacer part 8. When knee joint is about to be replaced with an artificial knee joint, usually the posterior cruciate ligament (PCL) remains in its normal state; and in such cases, the PCL is preserved. For that reason, the cut-out 8a is provided, and it is provided so as to not interfere with the PCL should it be preserved. Meanwhile, the reference pins 3 are pins that are inserted into the guide holes 9 of the reference pin guide 2 and installed into the resection plane of the end part of the distal end 4a of the femur 4. A set screw 10 is provided in the hollow box 7 to clamp therein the base 2a of the reference pin guide 2, and the hollow box 7 and the set screw 10 are indeed provided in front of and shifted from the tibia 5.

Figure 4:
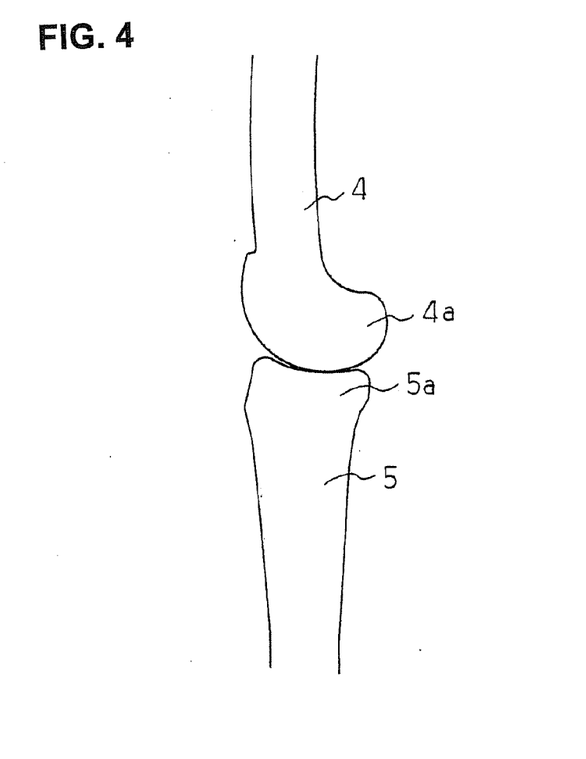
FIG. 4 An explanatory diagram showing a manner of resection in the extension position.
Figure 5:
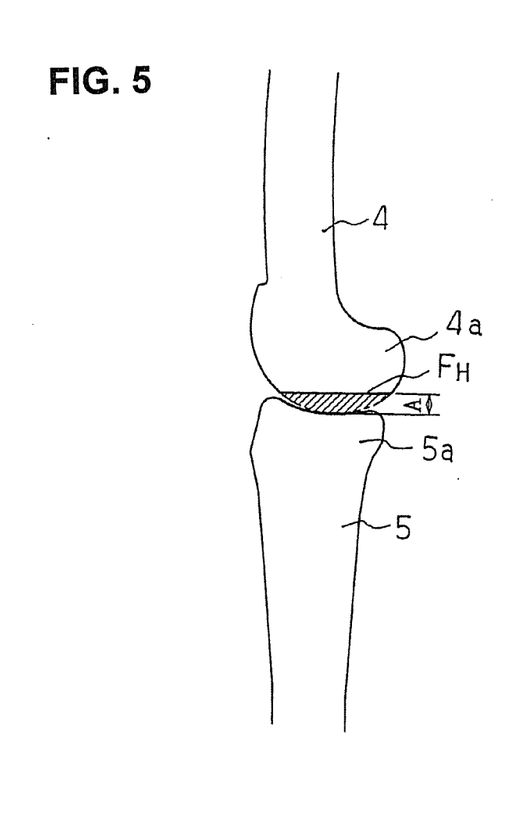
FIG. 5 An explanatory diagram showing a manner of resection in the extension position.
Figure 6:
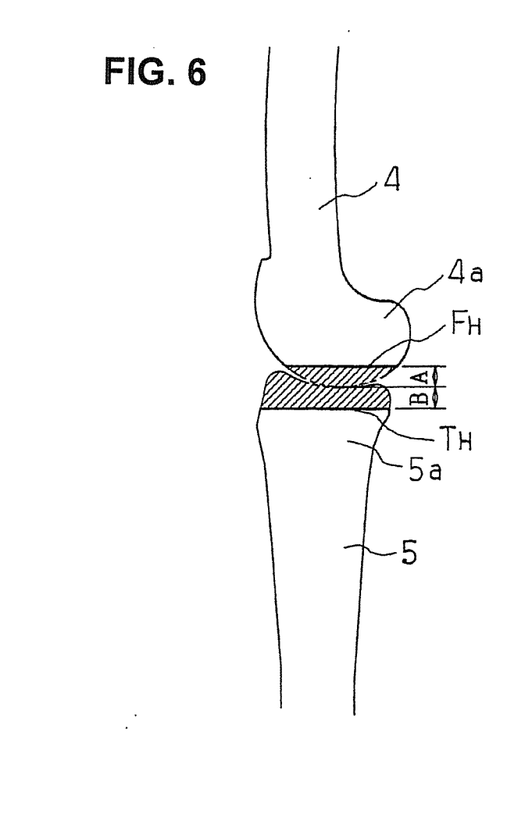
FIG. 6 An explanatory diagram showing a manner of resection in the extension position.
Figure 7:
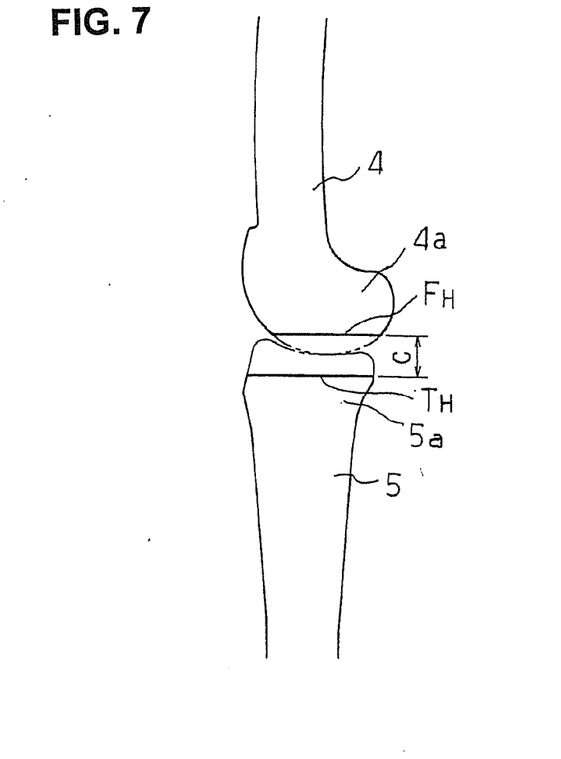
FIG. 7 An explanatory diagram showing a manner of resection in the extension position.

Next, surgery to replace a knee joint with an artificial knee joint using the various constituent parts described above will be described below with reference to FIGS. 4 through 7. The knee joint is at approximately 180° when it is in the extension position (FIG. 4). First, only a range A at the tip of the distal end 4a of the femur 4 is resected (FIG. 5). The extent of range A is determined by the surgeon in view of factors such as the severity of injury, age, body type, and the like. Then, only a range B at the tip of the proximal end 5a of the tibia 5 is resected (FIG. 6). While the extent of part B does depend on the severity of injury, it is also based on, considering the extent of range A, the shape and size of the artificial knee joint that is to be installed. By means of the above, a range A+B=C is resected at the tip of the distal end 4a of the femur 4 and the tip of the proximal end 5a of the tibia 5 (FIG. 7). In this case, the resection planes $F_H$ and $T_H$ of the femur 4 and the tibia 5, respectively, are normally made flat and parallel, and thus an appropriate jig (not shown) may be used during the resection process for this reason.

Figure 8:
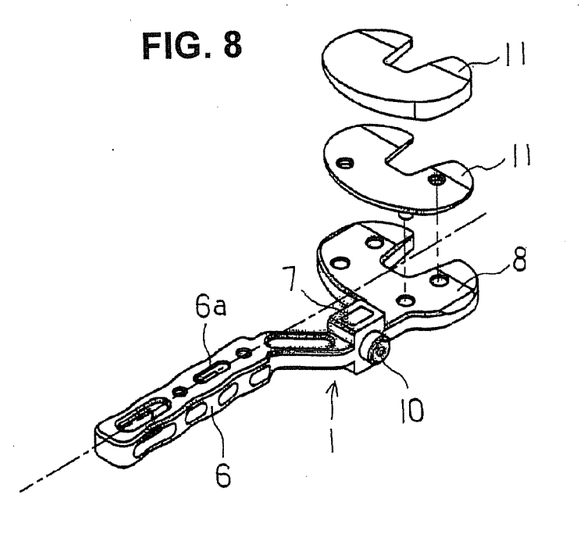
FIG. 8 A perspective view showing a relationship between the spacer block and the additional spacers.
Figure 9:
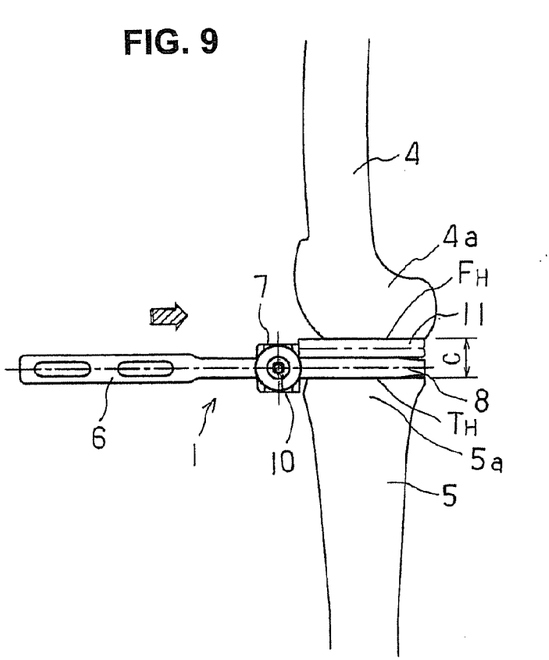
FIG. 9 A side view showing the spacer block inserted into the bone resection region of the femur and tibia in the extension position.

Then, in this state, the size of resection range C between the tip of the distal end 4a of the femur 4 and the tip of the proximal end 5a of the tibia 5 is checked to make sure that it is the value determined prior to the surgery (whether an artificial knee joint of a predicted shape and size can be installed, or what shape and size of an artificial knee joint is appropriate). To do this, in most cases, one or a plurality of additional spacers 11 are set one on top of the other on the reference spacer part 8 of the spacer block 1 (FIG. 8), and the resection range C between the femur 4 side and the tibia 5 side is measured from that thickness of the spacers; and then it is determined whether a predicted artificial knee joint can be used (FIG. 9). Incidentally, the additional spacers are set layered because the thickness of the reference spacer 8 alone is insufficient for the reasons that will be described below.

Figure 10:
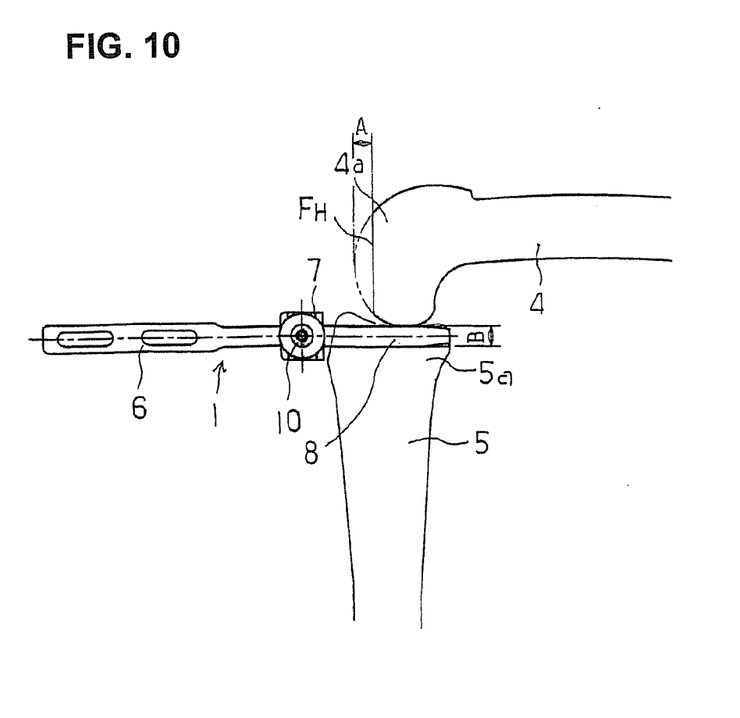
FIG. 10 A side view showing the spacer block inserted into the bone resection region of the femur and tibia in the flexion position.
Figure 11:
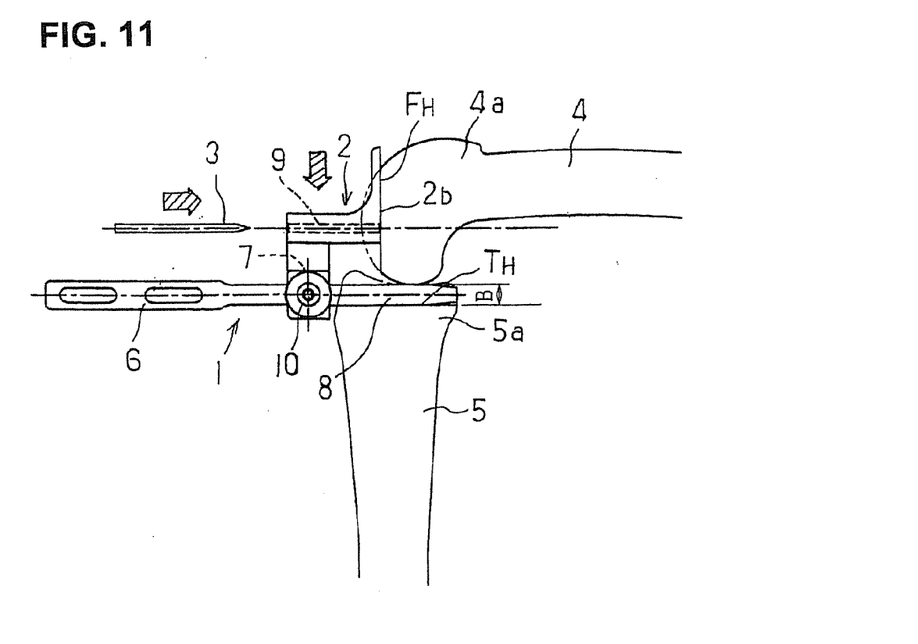
FIG. 11 A side view showing a manner of mounting the reference pin guide in the spacer block and of inserting the reference pins into the reference pin guide.

Once these matters have been confirmed, the additional spacers 11 are removed, and the femur 4 is placed in the flexion position (FIG. 10). The additional spacers 11 are removed because the back of the distal end 4a of the femur 4 is thick and the femur 4 cannot be placed into the flexion position with these spacers in place. However, since the reference spacer part 8 is made to be a thickness that can be inserted into the resection region C between the femur 4 side and the tibia 5 side with some margins, the femur 4 can be put into the flexion position when the spacers are removed. Next, the reference pin guide 2 is inserted into the vertical hole 7a of the spacer block 1 from above, and its back surface 2b is brought into contact with the resection plane $F_H$ of the tip of the distal end of the femur 4 (FIG. 11). This is done so as to bring the femur 4 into flexion of 90° relative to the tibia 5. The femur 4 can, nonetheless, be brought into an angle of greater than 90° flexion position to make deeper flexion possible; and so as to meet such a situation, the angle between the base 2a and back surface 2b of the reference pin guide 2 is set accordingly for such an angle. The reference pins 3 are then inserted into the guide hole 9 of the reference pin guide 2 and installed into the resection plane $F_H$ of the tip of the distal end of the femur.

Figure 12:
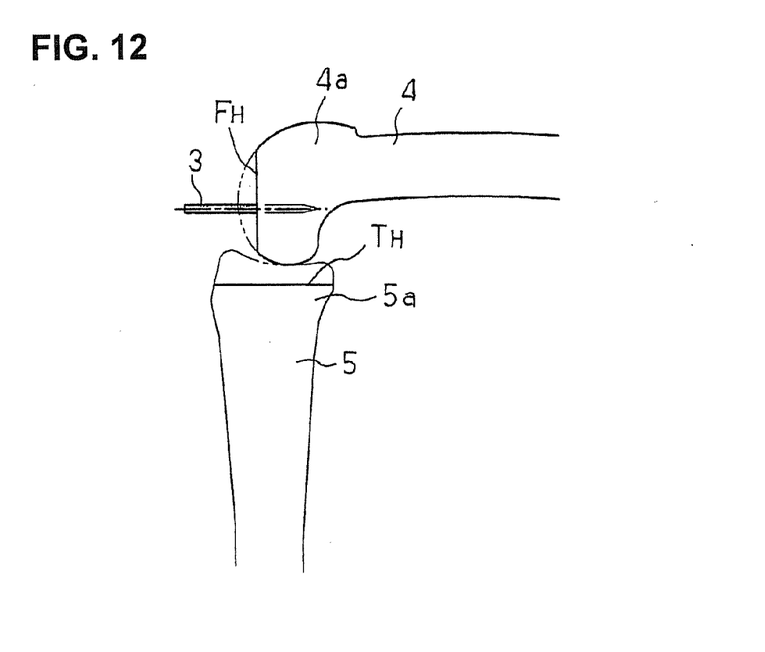
FIG. 12 A side view showing the reference pin guide removed from the spacer block.

Once the above is set, leaving the reference pins 3 in place, the spacer block 1 is, together with the reference pin guide 2, pulled out toward the front (FIG. 12). Then, the aiming member (sighting device) 12 is brought onto the reference pins 3 (FIG. 13) by being guided thereby. The aiming member 12 is of an square shape when seen from the front (FIG. 14), and it is provided with guide holes 13 into which the reference pins 3 can be inserted. The back surface 12b of the aiming member 12 is flat, and this back surface comes into contact with the resection plane $F_H$ of the tip of the distal end 4a of the femur 4. In the aiming member 12 is formed an indicator 14 that indicates the back resection plane $F_R$, which is formed by next resection position made to the distal end 4a of the femur 4.

Figure 13:
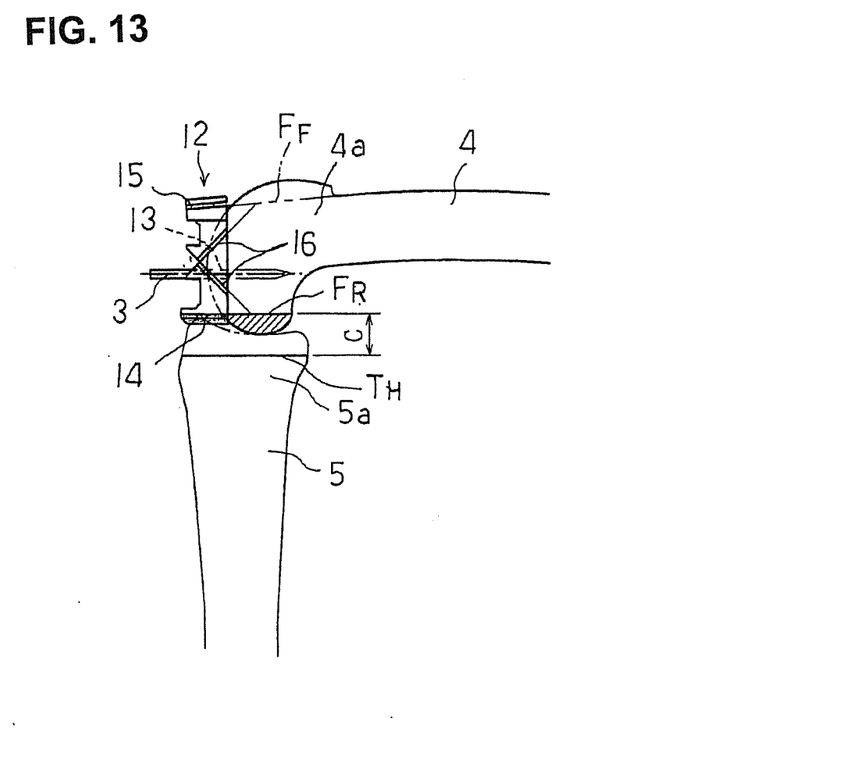
FIG. 13 A side view showing a sighting device installed on the reference pins as guides.
Figure 14:
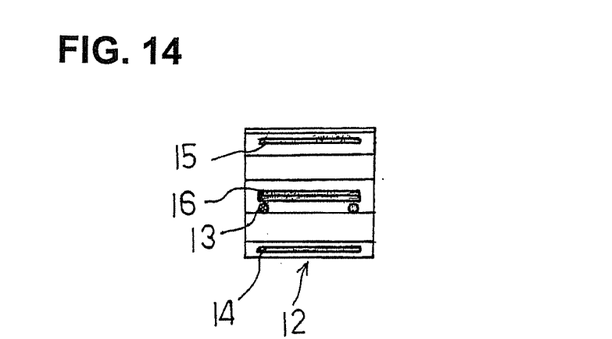
FIG. 14 A front view of the sighting device.

The indicator 14 is a small through-hole or an oblong through-hole (slit) through which cutters, scribes, gauges, drills and the like can be inserted. Thus, cutters or the like are inserted into the slit 14, and marks are made on a line that will be a preset resection plane $F_R$ on the back of the distal end 4a of the femur 4. By way of cutting the back along the marks as references, the back will be cut on a resection plane $F_R$. In this case, the resection plane $F_H$ of the tip of the distal end 4a of the femur 4 and the resection plane $F_R$ of the back of the distal end 4a of the femur 4 are substantially perpendicular with each other; however, they may be obtuse or acute angles depending on the shape and size of the artificial knee joint.

The aiming member 12 is further provided with a slit 15 that serves as an indicator for cutting the front portion of the femur 4, which is the next resection position of the distal end 4a of the femur 4. In other words, the slit 15 is formed above the aforementioned through-hole or oblong through-hole in the aiming member 12, and a cutter or the like is inserted through the slit 15, and marks are made on a line that will become the resection plane $F_F$ of the front of the distal end 4a. Then, resection is performed at resection plane $F_F$ along the marks. This resection plane $F_F$ is often inclined so that the top part is slightly higher than the resection plane $F_H$ of the tip (in an obtuse angle). This is to improve the installation characteristics to the femur component of an artificial knee joint.

Figure 15:
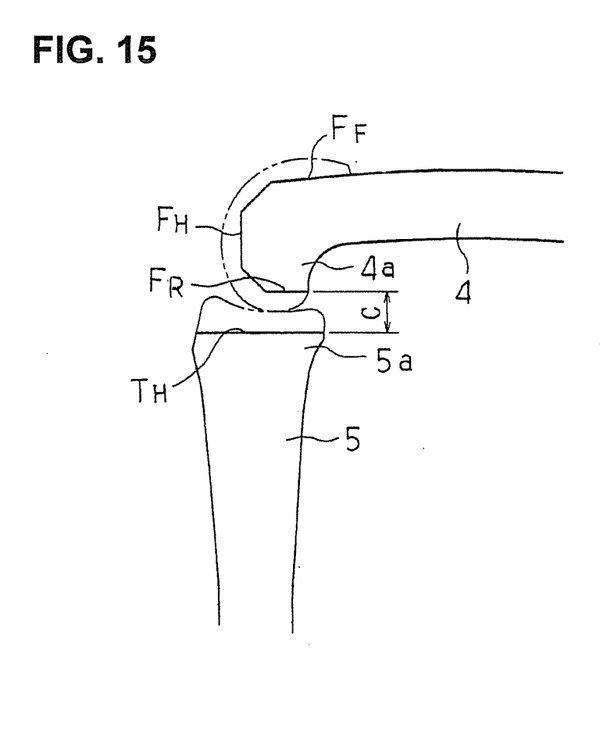
FIG. 15 A side view showing the back surface of the femur resected in the flexion position.

Furthermore, the aiming member 12 is provided with a slit 16 which is a hole and the like and formed so as to be inclined upward and downward to chamfer the corners of the resection planes $F_H$, $F_F$, and $F_R$. By way of cutting corners using the slit 16 as a guide, the bone is cut in a polygonal shape as shown in FIG. 15. This chamfering is to improve the installation characteristics to the femur component of an artificial joint. When the femur component and tibia component of an artificial joint are installed, the surgery ends. A variety of shapes and sizes may be selected for the femur component and the tibia component as described above depending on the severity of the injury, age, body type, and the like. The foregoing describes an artificial joint replacement for a right knee; and for a left knee use, the spacer block 1 can be flipped over.

DESCRIPTION OF REFERENCE NUMERALS

1 Spacer block
2 Reference pin guide
2a Base of the reference pin guide
2b Back surface of reference pin guide
3 Reference pins
4 Femur
4a Distal end of femur
5 Tibia
5a Proximal end of tibia
6 Grip
6a Hole in grip
7 Hollow box
7a Vertical hole of hollow box
8 Reference spacer part
8a Cut-out in reference spacer part
9 Guide holes
10 Connecting axis
11 Additional spacers
12 Aiming member
13 Insertion hole
14 Indicator (slit)
15 Indicator (slit)
16 Indicator (slit)

The invention claimed is:

1. A bone resection jig for an artificial knee joint replacement surgery, being used when a back of a distal end of a femur in a flexion position is resected after a tip of the distal end of the femur and a tip of a proximal end of a tibia in an extension position are resected horizontally, wherein the bone resection jig comprises:

a spacer block comprised of a grip, a hollow box that is provided on an other end side of the grip and has a vertical hole therein, and a reference spacer part that extends out from the hollow box and is adapted be inserted into the resection region between femur and tibia;

a reference pin guide which, when the femur and tibia are in the flexion position, is inserted into the vertical hole of the hollow box, extends on the reference spacer part to the other end side of the grip so as to come into contact with a resection plane of the tip of the distal end of the femur, and is formed with guide holes for guiding reference pins to be installed from a front side into the resection plane of the tip of the distal end of the femur; and an aiming member which is, after the spacer block has been removed in a front direction together with the reference pin guide from a space between the femur and tibia leaving the reference pins, brought onto the reference pins by being guided thereby, the aiming member being provided with an indicator that indicates a resection plane at a back of the distal end of the femur when the aiming member comes into contact with the resection plane of the tip of the distal end of the femur.

2. The bone resection jig used in artificial knee joint replacement surgery according to claim 1, wherein an axis of the grip passes through a center of the reference spacer part, and an area around the hollow box of the grip is offset with respect to the axis to place patellar tendon in a position not in interference.

3. The bone resection jig used in artificial knee joint replacement surgery according to claim 1, wherein the resection plane of the tip of the distal end of the femur is set at a right angle, obtuse angle or acute angle with respect to a resection plane of the back of the distal end of the femur.

4. The bone resection jig used in artificial knee joint replacement surgery according to claim 1, wherein two guide holes are provided horizontally left and right.

5. The bone resection jig used in artificial knee joint replacement surgery according to claim 1, wherein the indicators are through-holes or slits that are formed in the aiming member at a variety of levels and angles.

6. The bone resection jig used in artificial knee joint replacement surgery according to claim 1, wherein one or a plurality of additional spacers is layered on the reference spacer part for measuring a distance between a resected distal end of the femur and a resected proximal end of the tibia in the extension position.

7. The bone resection jig used in artificial knee joint replacement surgery according to claim 1, wherein said aiming member is further provided with:

an indicator that indicates a resection plane of a front of the distal end of the femur; and another indicator that is used for chamfering a corner of resection planes of the tip and the front of the distal end of the femur and chamfering a corner of resection planes of the tip and the back of the distal end of the femur.

* * * * *